United States Patent [19]
Hendricks et al.

[11] Patent Number: 5,580,970
[45] Date of Patent: Dec. 3, 1996

[54] DETECTION OF HPV TRANSCRIPTS

[75] Inventors: David A. Hendricks, Jamaica Plain; David J. Lane, Milford; Susan Rigby, Lexington; Kyriaki Parodos, Marlborough, all of Mass.

[73] Assignee: Amoco Corporation

[21] Appl. No.: 207,226

[22] Filed: Mar. 4, 1994

Related U.S. Application Data

[63] Continuation of Ser. No. 622,742, Dec. 5, 1990, abandoned, which is a continuation-in-part of Ser. No. 444,526, Dec. 1, 1989, abandoned.

[51] Int. Cl.$^6$ .............................. C07H 21/04; C12Q 1/70
[52] U.S. Cl. ............................................. 536/24.32; 435/5
[58] Field of Search ............................. 536/24.32; 435/5

[56] References Cited

U.S. PATENT DOCUMENTS

| | | | |
|---|---|---|---|
| 4,551,270 | 11/1985 | Danos et al. | 260/112.5 R |
| 4,849,331 | 7/1989 | Lorincz | 435/5 |
| 4,849,332 | 7/1989 | Lorincz | 435/5 |
| 4,894,334 | 7/1989 | Lorincz | 435/5 |
| 4,983,728 | 1/1991 | Herzog et al. | 436/501 |

FOREIGN PATENT DOCUMENTS

| | | | |
|---|---|---|---|
| 597698 | 6/1990 | Australia . | |
| 2002776 | 5/1990 | Canada | 435/5 |
| 0192001 | 8/1986 | European Pat. Off. | 435/5 |
| 0256321 | 2/1988 | European Pat. Off. | 435/5 |
| 0265244 | 4/1988 | European Pat. Off. | 435/6 |
| 0294659 | 12/1988 | European Pat. Off. | 435/6 |
| 0301968 | 1/1989 | European Pat. Off. | 435/5 |
| 0373352 | 6/1990 | European Pat. Off. . | |
| 0402132 | 12/1990 | European Pat. Off. | 435/5 |
| 2169403 | 7/1986 | United Kingdom . | |
| WO87/05630 | 9/1987 | WIPO | 536/27 |
| WO88/06634 | 9/1988 | WIPO | 435/5 |
| WO89/02934 | 4/1989 | WIPO | 435/6 |
| WO89/09940 | 10/1989 | WIPO | 435/5 |
| WO90/02821 | 3/1990 | WIPO | 435/5 |

OTHER PUBLICATIONS

Smotkin, D. and F. O. Wettstein, "Transcription of Human Papillomavirus Type 16 Early Genes in a Cervical Cancer and a Cancer–Derived Cell Line and Identification of the E7 Protein", *Proc. Natl. Acad. Sci. USA*, vol. 83, pp. 4680–4684 (Jul. 1986).

Schneider–Gädicke, A. and E. Schwarz, "Different Human Cervical Carcinoma Cell Lines Show Similar Transcription Patterns of Human Papillomavirus Type 18 Early Genes", *EMBO J.* 5(9): 2285–2292.

W. K. Chan et al., *Annals of the Academy of Medicine, Singapore*, 17(2): 232–237 (Apr. 1988).

C. P. Crum et al., In: *Viruses and Human Cancer*, R. C. Gallo et al, (Eds.), Alan R. Liss, Inc., New York, pp. 335–369 (1987).

Cole, S. T. and O. Danos, *J. Mol. Biol.*, 193: 599–608 (1987).

Cole, S. T. and R. E. Streeck, *J. Virol.*, 58(3): 991–995 (1986).

Goldsborough et al., *Virology*, 171: 306–311 (1989).

Seedorf et al., *Virology*, 145§ 181–185 (1985).

Manos et al., (1989), In: *Cancer Cells, vol. 7, Molecular Diagnostics of Human Cancer*, M. Furth and M. Greaves, Eds., Cold Spring Harbor Laboratory Press, Cold Spring Harbor, NY, pp. 209–214 "Use of Polymerase Chain Reaction Amplification for the Detection of . . . ".

Shibata, D. K. et al., *J. Exp. Med.*, 167: 225–230 (1988) "Detection of Human Papilloma Virus in Paraffin–Embedded Tissue Using the Polymerase Chain Reaction".

Ionesco, M. et al., *Bull. Cancer*, 74: 397–406 (1987) (Summary: Correlation between histologic features and the presence of different human papillomavirus types in cervical lesions.)

*Primary Examiner*—Stephanie W. Zitomer
*Attorney, Agent, or Firm*—Norval B. Galloway

[57] ABSTRACT

A method for detecting and/or quantitating specific DNA and/or RNA transcripts of human papillomavirus (HPV) is described. Nucleic acid probes specific for DNA or transcripts are used to determine the amount of the DNA or transcripts, and to ascertain the degree of amplification of certain high-oncogenic HPV genes. The method provides an accurate and reliable method for prognosticating serious cervical neoplasias and cancers.

7 Claims, 8 Drawing Sheets

FIGURE 3

| HPV Probe No. | | Oligonucleotide Sequence | | | Target Nts. | |
|---|---|---|---|---|---|---|
| | | 5' | | 3' | | |
| 6 | | | | | | |
| | 6-1 | ACAACTGGTC | TATGGTCGTT | GCAGACGTGG | AGGCATTTGC | 111-150 |
| | 6-2 | TTGCAAAACA | CACAATTAAT | TTGCAACGTA | TGCATAGAT | 167-205 |
| | 6-3 | TTTAAAGGTT | GTGAATCTTG | TCCGTCCACT | TC | 644-675 |
| | 6-4 | GTTTCTGTAC | ACTGCACAAC | CAGTCGAACG | TTGCTG | 715-750 |
| | 6-5 | TATGTTTAGT | GTTCCCAACA | GAAGCTGTTG | CACTTC | 761-796 |
| 11 | | | | | | |
| | 11-1 | CTCAACTGGT | CTATAGATGT | TGCAGACGTG | GAGGCATCTT | 112-151 |
| | 11-2 | CTGAATTTGC | AGAGTGTGCA | AAGAAAGATT | AAACGTCTTG | 152-191 |
| | 11-3 | TGTAACCCTA | CAGGGTCAGG | AGGCCAGG | TCTAGTACTA | 561-600 |
| | 11-4 | CCACAGCAAC | AGGTCAGTAT | TTGGTAATGT | TGTGTTAAAG | 669-708 |
| | 11-5 | CCGTCTGTGC | ACTCCACAAC | CAGTCGGACG | TTGCTG | 715-750 |
| | 11-6 | TATTTAGTGT | GCCCAGCAAA | AGGTCTTGTA | GTTGTCTGAT | 755-794 |
| 16 | | | | | | |
| | 16-1 | TCTGGGTCGC | TCCTGTGGGT | CCTGAAACAT | TGCAGTTCAT AT | 96-133 |
| | 16-2 | TCTAATATTA | TATCATGTAT | AGTTGTTTGC | AGCTCTGTGC | 150-189 |
| | 16-3 | TGGCAACAAA | AGGTTACAAT | ATTGTAATGG | GCTCTGTCCG | 701-740 |
| | 16-4 | GTCTACGTGT | GTGCTTTGTA | CGCACAACCG | AAGCGTAGAG | 747-786 |
| | 16-5 | TTCCTAGTGT | GCCCATTAAC | AGGTCTTCCA | AAGTACGAAT | 787-826 |
| 18 | | | | | | |
| | 18-1 | GTAGGGTCGC | CGTGTTGGAT | CCTCAAAGCG | CGCCATAG | 103-140 |
| | 18-2 | GTTATTTCTA | TGTCTTGCAG | TGAAGTGTTC | AGTTCCGTGC | 157-196 |
| | 18-3 | TAGAAGGTCA | ACCGGAATTT | CATTTTGGGG | CTCTAAATGC A | 627-667 |
| | 18-4 | TTACAACACA | TACACAACAT | TGTGTGACGT | TGTGGTTC | 752-789 |
| | 18-5 | GTCGTCTGCT | GAGCTTTCTA | CTACTAGCTC | AATTCTGGCT | 796-835 |
| | 18-6 | AGGACAGGGT | GTTCAGAAAC | AGCTGCTGGA | ATGCTCGAAG | 836-875 |
| 31 | | | | | | |
| | 31-1 | CAATTTCCGA | GGTCTTTCTG | CAGGATTTTT | GAACATGGCG | 103-142 |
| | 31-2 | GTTCATCGTA | GGGTATTTCC | AATGCCGAGC | TTAGTTCATG | 145-183 |
| | 31-3 | ACGAAGTGTA | GACTTACACT | GACAACAAAA | GGTAACG | 721-757 |
| | 31-4 | CTCTTGCAAT | ATGCGAATAT | CTACTTGTGT | GCTCTGTACA | 763-802 |
| | 31-5 | CAGTCTAGTA | GAACAGTTGG | GGCACACGAT | TCCAAATGA | 815-853 |
| 33 | | | | | | |
| | 33-1 | ATGCTTGGCA | CAAATCATGC | AATGTTCGTG | GTTTTCCTC | 124-163 |
| | 33-2 | TTCCACGCAC | TGTAGTTCAA | TGTTGTGTAT | AGTTGTCTCC A | 164-204 |
| | 33-3 | GTATAGGTCA | GTTGGTTCAG | GATATAAATC | TAAAACATAT | 602-641 |
| | 33-4 | AGTGTGACAA | CAGGTTACAA | TGTAGTAATC | AGCTGTGGCT | 713-752 |
| | 33-5 | TTGCTGTACT | GTTGACACAT | AAACGAACTG | TGGTGTT | 756-792 |
| | 33-6 | TATTCACTGT | GCCCATAAGT | AGTTGCTGTA | TGGTTCGTAG | 798-837 |
| 35 | | | | | | |
| | 35-1 | TAAGGTCGTT | CAGCTGGGTC | CTGAAACATA | CCGCACCTT | 111-149 (SEQ ID NO:1) |
| | 35-2 | CATGGATGCT | TTCTTCTACC | TCGTTGCACA | AATCATGCAG T | 153-193 (SEQ ID NO:2) |
| | 35-3 | CACAGACGTA | GTGTCGCCTC | ACATTTACAA | CAGGACGTT | 740-778 (SEQ ID NO:3) |
| | 35-4 | ATCTTCCAAT | TTACGTATGT | CAATGTGTGT | GCTCTGTACT | 780-818 (SEQ ID NO:4) |
| | 35-5 | CTCTCTGTGA | ACAGCCGGGG | CACACTATTC | CAAATGTGCT | 829-867 (SEQ ID NO:5) |

FIGURE 6

```
Probe 16-3    3'    GCCTGTCTCGGGTAATGTTATAACATTGGAAAACAACGTT           5'

HPV 16   5'    CGGACAGAGCCCATTACAATATTGTAACCTTTTGTTGCAA           3'
              nt    701                                       740

HPV 6          CtttaAaAcaaCATTtCcAaATaGTgACCTgTTGcTGtgg
     HPV 11         CtttaAcAcaaCATTACcAaATacTgACCTgTTGcTGtgg
     HPV 18         gaaccAcAacgtcacACAATgTTGTgtatgTgTtgTaagt
     HPV 31         CGGACAcAtCCaATTACAATATcGTtACCTTTTGTTGtcA
     HPV 33         CAGcCAcAGCtgATTACtAcATTGTAACCTgTTGTcaCAc
     HPV 35         CaGACAcctCCaATTAtAATATTGTAACgTccTGTTGtAA           (SEQ ID NO:6)

Probe 16-4    3'    GAGATGCGAAGCCAACACGCATGTTTCGTGTGTGCATCTG           5'

HPV 16   5'    CTCTACGCTTCGGTTGTGCGTACAAAGCACACACGTAGAC           3'
              nt    747                                       786

HPV 6          CagcAacgTTCGacTGgttGTgCAgtGtACAgAaacAGAC
     HPV 11         CagcAacgTcCGacTGgttGTggAgtGCACAgACGgAGAC
     HPV 18         agCcAgaaTTgaGcTagtaGTAgAAAGCtCAgcaGacGAC
     HPV 31         gTCTACaCTTCGtTTGTGtGTACAgAGCACACAaGTAGAt
     HPV 33         caCcACagTTCGtTTaTGtGTcaAcAGtACAgcaagtGAc
     HPV 35         ggCgACaCTaCGtcTGTGtGTACAgAGCACACACaTtGAC           (SEQ ID NO:7)

Probe 16-5    3'    TAAGCATGAAACCTTCTGGACAATTACCCGTGTGATCCTT           5'

HPV 16   5'    ATTCGTACTTTGGAAGACCTGTTAATGGGCACACTAGGAA           3'
              nt    787                                       826

HPV 6          ATcaGagaagTGcAAcAgCTtcTgtTGGGaACACTAaacA
     HPV 11         ATcaGacaacTacAAGACCTttTgcTGGGCACACTAaatA
     HPV 18         cTTCGagcaTTccAgcAgCTGTTtcTGaacACcCTgtccT
     HPV 31         ATTCGcAtaTTGcAAGAgCTGTTAATGGGCtCAtTtGGAA
     HPV 33         cTacGaACcaTacAgcAacTacTtATGGGCACAgTgaatA
     HPV 35         ATaCGTAaaTTGGAAGAttTaTTAATGGGCACAtTtGGAA           (SEQ ID NO:8)
```

DETECTION OF HPV TRANSCRIPTS

DESCRIPTION

Related Applications

This application is a continuation of application Ser. No. 07/622,742, filed Dec. 5, 1990, now abandoned, which is a continuation-in-part of U.S. application Ser. No. 07/444,526, by D. Hendricks, D. Lane and Susan Rigby, filed Dec. 1, 1989 and now abandoned, the entire disclosure of which is incorporated herein by reference.

BACKGROUND

Epidemiologic data are accumulating which show that the human papillomavirus (HPV) is strongly associated, as a factor or co-factor, with cervical cytologic abnormalities, such as cervical intraepithelial neoplasias (CIN) and carcinoma in situ (CIS). Syrjanen, K. J., *In: Papillomaviruses and Human Disease*, K. Syrjanen, L. Gissman, and L. G. Koss (Eds.), Springer-Verlag, pp 467–503, (1987). In general, these dysplasias are found in the transition zone of the cervix and are graded from mild to severe (I to III), based on the extent to which neoplastic cells extend from the basal layer to the epithelial surface. Complete replacement of the epithelium by neoplastic cells is termed carcinoma in situ (CIS).

At least 60 types of HPV, isolated from various parts of the human body, have been documented, and more than 20 of these types have been shown to be associated with the genital mucosa. E. M. de Villiers, *J. Virol.*, 63(11):4898–4903 (1989). Although present information strongly supports the close association between HPV and cervical neoplasia, and shows that many individuals clearly have HPV DNA (i.e., infections), transiently and/or latently, it also makes it clear that women in whom HPV is present in cervical cells do not always progress to more serious dysplasia. Syrjanen et al. in *Cancer Cells*, Vol. 5, Cold Spring Harbor, pp. 281–288 (1987); deBrux et al., *Bull. Cancer (Paris)*, 70:410–422 (1983); Mitchell et al., *The Lancet*, 1:573–575 (1986). Thus, simple detection of HPV DNA in cervical specimens lacks discriminatory predictive value for identification of women at risk for serious disease. A method for assessing HPV activity which can be used to predict progression to serious CIN or CIS is needed.

SUMMARY OF THE INVENTION

The present invention relates to a method for detecting and quantitating specific transcripts of HPV and/or HPV DNA in cervical specimens and, in addition, to a method of determining patterns of HPV transcription which are more reliable indicators or predictors of the risk of progression to serious dysplasia or cervical carcinoma in individuals in whom HPV is present than is measurement of total HPV DNA in a sample. The method involves detecting and/or quantitating RNA, DNA or RNA/DNA ratios which are indicative of the presence or absence of high-oncogenic types of HPV. For example, one embodiment of the method involves using nucleic acid probes and/or probe sets comprising DNA or RNA sequences which hybridize to transcripts of the E6 and/or E7 genes of specific HPV types, particularly to HPV types associated with oncogenesis, referred to as high-oncogenic HPV types, (e.g., HPV 16, 18, 31, 33, 35, 39, 45, 51, 52 and 56), but not to low-oncogenic HPV types (e.g., HPV 6 and 11).

The present method can also be used to detect and/or quantitate low-oncogenic HPV types (e.g., HPV 6 and HPV 11), if desired (e.g., as an indication of lower risk of progression to serious CIN or CIS in an individual having an HPV infection than would be the case if high-oncogenic HPV types are present).

The present method is based on hybridization of selected nucleic acid probes for detection and/or quantitation of specific HPV messenger RNAs (mRNAs) or DNA; thus it provides a means for assessing active transcription of the HPV genome.

Type-specific nucleic acid probes and probe sets for HPV are also the subject of the present invention. These probes are of two types: polynucleotide-tailed oligonucleotide capture probes and labelled detector probes (also referred to as labelled riboprobes). Tailed capture probes serve two purposes: 1) they hybridize to at least a portion of an open reading frame (ORF) sequence of an HPV gene or to at least a portion of the encoded transcript of a selected HPV type which is associated with abnormalities, progression to higher grade CIN or development of CIS in cervical epithelial cells; and 2) they link (through the polynucleotide tail) the hybridization complex formed as a result of the method described to a solid support, thus making it possible to separate the hybridization complex from the remainder of the sample. Labelled detector probes are generally single-stranded RNA molecules or single stranded DNA molecules which hybridize to portions of bi- or polycistronic transcripts of genes associated with cervical cytologic abnormalities, such as the E6 and/or E7 genes, or to spliced transcripts which contain these ORF's or portions thereof, of selected HPV types; specifically, labelled detector probes form stable hybrids with these transcripts, including spliced transcripts. Although it is possible to use detector probes which hybridize to target sequences which also are recognized by capture probes, it is preferable that they do not. In addition, probes for specific detection of spliced transcripts of the E6 gene of HPV 16, HPV 18, HPV 31, HPV 33 and HPV 35 are the subject of the present invention. Such probes are splice-junction capture probes designed to form stable hybrids only with spliced transcripts of a selected HPV type and they serve as examples of a class of probes which are useful in the present method.

A method for determining prognosis in individuals infected with HPV is also the subject of the present invention. The method is based on the association between HPV transcriptional activity and the risk for development of serious cervical dysplasia or carcinoma. For example, patterns and/or levels of transcription of at least a portion of the E6 and/or E7 genes and spliced downstream sequences of selected high-oncogenic HPV types can be used to predict the progression of HPV infection to serious CIN or CIS. Conversely, patterns and/or levels of transcription of the E6 or E7 genes of low-oncogenic HPV types can be used as an indication of reduced risk of serious CIN or CIS. Thus, the detection of E6 and/or E7 transcripts of selected HPV types in cervical samples provides a more valuable diagnostic aid than mere detection of HPV DNA.

Certain patterns of HPV transcription can provide a more reliable indicator of risk for progression to serious dysplasia than does detection of total HPV DNA. Low levels of HPV DNA are quite prevalent in women and, thus, the presence of HPV DNA is not a sensitive measure of neoplastic risk. The detection and quantitation of transcripts of genes associated with high-oncogenic or low-oncogenic types of HPV, and/or spliced mRNAs containing these sequences provide a sensitive, accurate, reliable prognosticator of serious dysplasia or cancer.

BRIEF DESCRIPTION OF THE FIGURES

FIG. 3 shows the nucleotide sequences of thirty-three type-specific oligonucleotide probes, which range in length from 32 to 41 nucleotides.

FIG. 6 shows nucleotide sequences of possible base pairs between HPV 16 capture probes 16-3, 16-4, and 16-5 and aligned sequences in the E7 ORF's of HPV 6, HPV 11, HPV 18, HPV 31, HPV 33 and HPV 35. Bases in upper case are predicted to form base pairs with the oligonucleotide probe.

FIG. 8A shows typical results from the HPV 16 assay using a $^{32}$P-labeled detector probe with a specific activity of $5 \times 10^8$ cpm/µg. FIG. 8B is a graph showing the linear relationship between the concentration of positive target and the amount of signal.

DETAILED DESCRIPTION OF THE INVENTION

Figure 1:
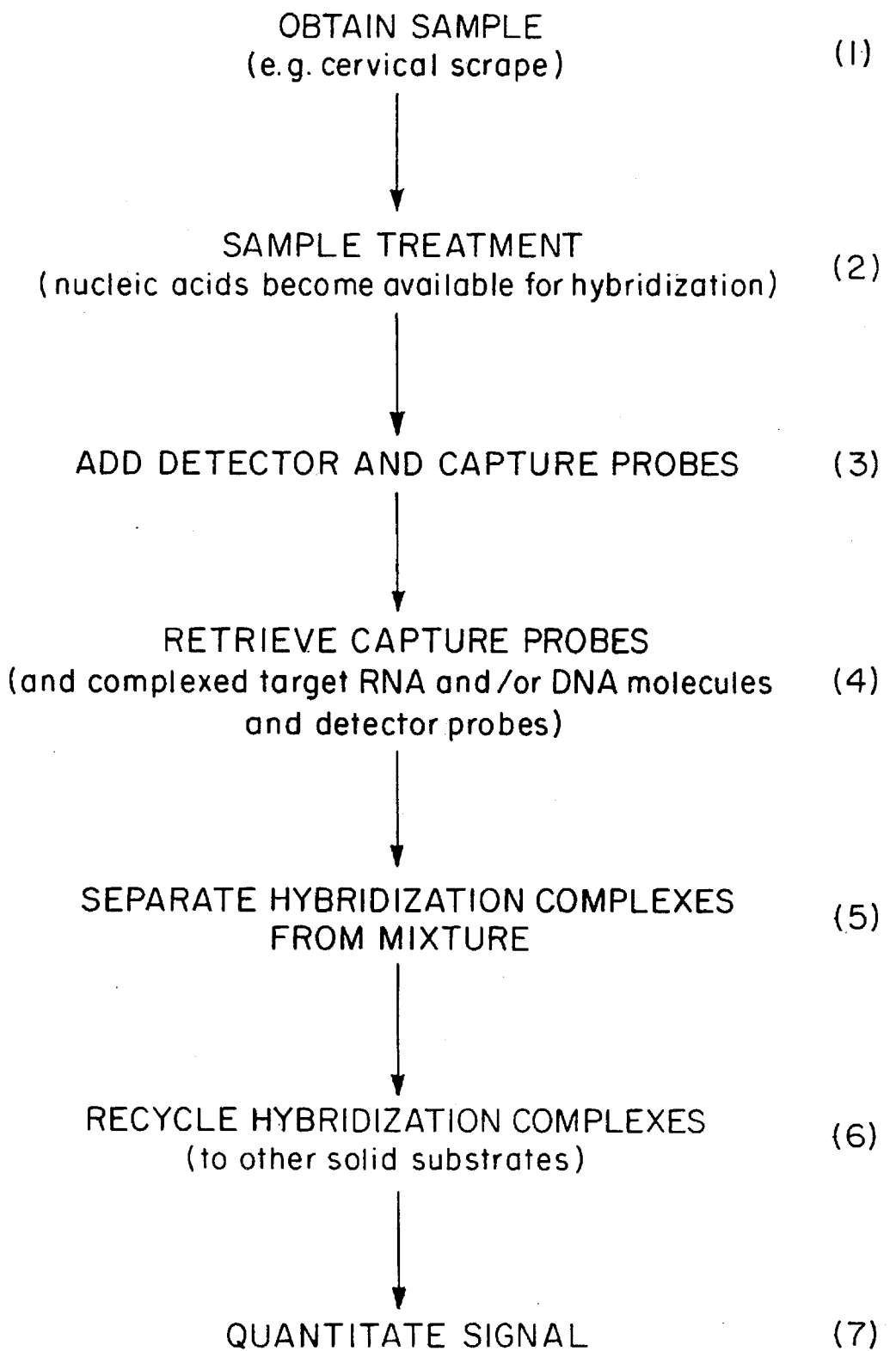
FIG. 1 is a schematic representation of the method of the present invention.

The present invention is based on an understanding of the close association between HPV and cervical carcinoma; the fact that although many individuals have HPV DNA in cervical cells, they do not progress to more serious dysplasia; and a determination that simple detection of HPV DNA in cervical specimens appears to lack discriminatory predictive value for identification of individuals at risk for progression to serious disease.

In contrast to commonly used techniques for detection of HPV DNA, the present method allows sensitive and quantitative detection of specific HPV mRNA or DNA. The present method makes it possible to assess active transcription of the HPV genome and to determine the associations between HPV transcription patterns and risk for development of cytopathology and/or progression to more serious disease (i.e., higher grade CIN or CIS) in HPV-infected individuals. The following is a brief summary of the assessment of the role of HPV in cervical abnormalities, which establishes the need, and therefore the utility of the present method, a detailed description of the method, a description of HPV-specific nucleic acid probes useful in the method, and discussion of an application of the method in a clinical context for diagnostic and/or therapy-related purposes.

The Role of HPV in Cervical Abnormalities

The role of HPV in cervical abnormalities, which range in severity from mild dysplasia to complete replacement of the cervical epithelium (CIS), has been studied extensively.

A positive correlation between grade of dysplasia (i.e., CIN I, II or III and CIS) and the presence of HPV has been established. Kurman et al., Am. J. Obstet. Gynecol., 159:293–296 (1988); Koutsky et al., Epidem. Rev., 10:122–163 (1988); deVilliers et al., The Lancet, 2:703–706 (1987). It has been determined that higher grade cytologic abnormalities are more often associated with HPV types 16, 18, 31 and 33 than with low-oncogenic HPV types. HPV types 6, 11, 16 and 18 are found in 80–90% of dysplasias. Koutsky et al., ibid.

However, HPV DNA also has been shown to be present in cervical samples evidencing no abnormality. For example, assays of cervical specimens for HPV DNA of types 6, 11, 16 and 18 by polymerase chain reaction (PCR) from 150 women with no cytologic abnormalities revealed that HPV DNA was present in 70–84% of the women. Young et al., British Med. J., 298(6665):11–14 (1989); Tidy et al., The Lancet, (Feb. 25, 1989) p. 434.

Relatively long-term epidemiologic studies which assess clinical progression from HPV-associated infections (koilocytosis and/or HPV DNA) to CIN I or greater suggest that 8–15% of HPV infections became more dysplastic with time. Syrjanen, K. et al., Papillomaviruses: Cancer Cells, Vol. 5, Cold Spring Harbor, pp 281–288, (1987); de Brux et al., Bull Cancer (Paris), 70:410–422, (1983); Mitchell et al., The Lancet, 1:573–575, (1986); Syrjanen, K. et al., J. Cellular Biochem., Suppl., 13C, p.198 (1989). Conversely, this suggests that 85–92% of HPV infections do not progress with time. Progression was observed more frequently (about 35%) in individuals infected with HPV 16 than with types 6, 11, 18, 31, and 33 (7.5%–20%). It is unclear, at least, and unlikely, at best, that the presence of HPV DNA alone is a prognostic indicator of progression to serious dysplasias, at least in part because co-factors very likely play roles in disease progression.

Several lines of evidence suggest that expression of the E6 and/or E7 genes of HPV is necessary for oncogenesis. The expression of these genes causes transformation of rat or mouse epithelial or fibroblast cells (Crook et al., Proc. Nat'l. Acad. Sci., 85:8820–8824 (1988); Watanabe and Yoshiike, Int'l. J. Cancer, 41:896–900 (1988)), and, after insertion into a retroviral vector, produces tumors in nude mice. Yutsudo et al., Virol., 166:594–597 (1988). Other investigators showed that the E7 gene can cooperate with an activated ras oncogene to transform primary baby rat kidney cells and can transactivate a heterologous viral promoter. They also showed that portions of the predicted E7 protein are similar to several of the conserved domains of the adenovirus E1a protein, a transactivating protein which can also cooperate with an activated ras oncogene to transform rat epithelial cells. Furthermore, continued expression of the E7 gene seems to be required for maintenance of the transformed phenotype in cells which have been transformed by HPV 16 and EJ-ras Banks et al., J. Cellular Biochem., Suppl. 13C:202 (1988); Crook et al., EMBO Journal, 8(2):513–519 (1989). The E7 protein is localized in the cytoplasm and has been shown, by Western blot analysis, to be the most abundant HPV protein in cell lines containing HPV 16 DNA (CaSki and SiHa) or HPV 18 (HeLa, C4-1, and SW756). Seedorf et al., *EMBO J.*, 6(1):139–144 (1987).

In all HPV-containing cervical carcinomas, and cell lines derived from them, the E6 and E7 genes are intact. Wilzynski et al., *Virol.*, 166:624–627 (1988). Furthermore, transcripts of the E6 and/or E7 gene, but not necessarily other early genes, are consistently found in carcinomas and carcinoma cell lines. Baker et al., *J. Virol.*, 6(1):962–971 (1987); Pater and Pater, *Cancer Res.*, 48:324–328 (1988); Schneider-Gadicke and Schwarz, *EMBO Journal*, 5(9):2285–2292 (1986); Schwarz et al., *In: Papillomaviruses and Human Disease,* Springer-Verlag, pp. 443–466 (1987); Shirasawa et al., *J. Gen. Virol.*, 68:583–591 (1987); Smotkin and Wettstein, *Proc. Nat'l Acad. Sci.*, 83:4680–4684 (1986). The evidence suggests that expression of the E6 and/or E7 genes of HPV 16 and 18 are important for cellular transformation and may be important to the development of CIS.

Thus, although presently-available data suggest a strong association between HPV DNA in cervical samples and cervical abnormalities which range in severity from mild dysplasia to CIS, they also make it clear that many, and perhaps most, women in whom HPV DNA is present in cervical samples do not progress to dysplasia.

Patterns of transcription, including spliced transcripts, have been examined for several HPV types with high oncogenic potential. Examination of three cell lines containing HPV 18 has shown three patterns of transcription (ascertained by analysis of cDNA clones). Schwarz et al., *Nature*, 314:111–114 (1985). Pattern 1 contains full length transcripts of the E6 and E7 genes and the 5'-terminal 11 nucleotides (nts) of the E1 RNA (E1 starts at nt 914; splice donor site at nt 925) spliced to 3' cellular sequences. Patterns 2 and 3 contain shortened transcripts of E6 (intron of 182 nts missing between a splice donor site at nts 226–234 and the splice acceptor site at nts 401–412), designated E6*, which are joined to sequences of E7 and either downstream cellular sequences (Pattern 2) or to downstream HPV sequences. (Pattern 3). E6* splice sites also are present in DNA sequences of HPV 16, HPV 31, HPV 33, HPV 35, HPV 43, HPV 52 and HPV 56 but not in DNA of low-oncogenic HPV types (i.e., 6 and 11) Goldsborough et al., *Virol.*, 171:306–311 (1989). Therefore, the E6* transcripts may be related to oncogenic potential of the HPV types. E6/E6* and E7 transcripts are found in HPV 16-containing cells, but they also contain spliced downstream E2-E4 exons, followed by cellular sequences. Two HPV 16 E6* transcripts have been identified in SiHa cells and two cancers. Smotkin et al, *J. Virol.* 63(3):1441–1447 (1989). Both of them use a common donor splice site at nts 224–232 and a splice acceptor site at either nts 399–417 (E6*I) or at nt 516–543 (E6*II). Because translation of E6*I terminates at a greater distance from the E7 translation start signal (AUG) than does translation termination of E6*II, the former transcript may allow more efficient translation of the E7 ORF.

Such transcription patterns described above form the basis for the design of probes and for their use in the method of detection and/or quantitation of specific transcripts of HPV in samples in the present invention. In addition, they provide the basis by which the present method is used for assessing risk of progression of cervical abnormalities. They provide the basis by which the present method is employed to detect and/or quantitate the above-described transcription patterns and/or other transcription patterns for assessing risk of progression of cervical abnormalities to more serious disease. As will be explained and illustrated, the present method is one in which RNA, DNA or the ratio of RNA to DNA of specific HPV types in cervical samples are detected and/or quantitated as a measure of neoplastic risk. Detection and/or quantitation of E6, E7 and spliced transripts of HPV types associated with oncogenesis or progression of cervical dysplasias as a means of determining neoplastic risk provides a novel tool which can be used not only in a diagnostic context (i.e., to assess presence or absence of risk of progression), but also in a therapeutic context (i.e., as a means by which treatment can be designed and/or monitored).

Detection of Specific HPV Transcripts by the Present Method

The present method specifically involves detection and/or quantitation of RNA of selected HPV types which are associated with oncogenesis. In particular, the expression of the E6 and/or E7 genes, which can include downstream genes, and their expression relative to other genes is believed to be a prerequisite for HPV-related oncogenesis. In one embodiment of the present method, HPV transcription levels, particularly transcripts of at least a portion of the E6 and/or E7 genes of selected HPV types, are measured. That is, the amount of E6 and/or E7 mRNA present in a sample is detected and quantitated. Bicistronic and/or spliced transcripts of these genes also can be measured.

The Method of the Present Invention

The present invention is a nucleic acid hybridization method which makes use of two types of nucleic acid probes, each of which is complementary in sequence to and capable of hybridizing to at least a region of the RNA transcript of the gene of at least one HPV type associated with oncogenesis or to an HPV gene. In particular, HPV DNA or HPV mRNA transcripts expressing at least a portion of the E6 and/or E7 genes, are detected and/or quantitated using the method.

The method is represented schematically in FIG. 1 and is described below as it can be applied to any selected HPV type. It is further described, with reference to a specific HPV type (HPV 16). The sample to be assayed by the present method for E6/E7 and other spliced mRNA transcripts will generally be, for example, a cervical scrape, smear, mucus specimen, biopsy or tumor specimen. The sample does not have to be separated, filtered or precultured prior to being assayed by the present method. The sample can be mixed or diluted in a medium, if appropriate, and, if necessary, pretreated with an agent which disrupts cell and molecular structures within the cells. This disruption step frees the nucleic acids to be detected (the target nucleic acids). Cells can be disrupted, for example, using chaotropic agents which disrupt the molecular structure of a cell. That is, the agent denatures the secondary, tertiary and/or quaternary structures of biopolymers, including proteins, nucleic acids and polysaccharides, which are generally found in biological specimens. Examples of chaotropic agents include chaotropic salts (e.g., guanidinium thiocyanate), hydrolyric enzymes (e.g., proteases, RNAases) and compounds that disrupt hydrophobic interactions (e.g., sodium dodecyl sulfate, phenols, dimethylformamide, dimethyl sulfoxide, tetramethyl urea or guanidinium hydrochloride). Physical or mechanical means of disrupting molecular structures, e.g., sonication, can also be used to release nucleic acids. If necessary, nucleic acids present in the cells and released from the cells are also treated to render them available for hybridization with complementary nucleic acid sequences (e.g., by heating to render double stranded sequences single stranded).

Two types of HPV type-specific probes are then contacted with the sample, either simultaneously or sequentially. One is the HPV type-specific tailed capture probes, which can be free or bound to a solid support. The capture probes are allowed to hybridize with the target transcripts in the sample mixture, forming a capture probe/target transcript complex. Either along with the capture probe or after the capture probe/target transcript complex is formed, labeled detector probes are also contacted with the sample, which is maintained under appropriate conditions (e.g., time, temperature, pH, salt concentration, chaotrope concentration) for hybridization of complementary nucleotide sequences to occur and form a capture probe/target transcript/detector probe complex. The capture probe/target transcript/detector probe complex, which, for convenience, is subsequently referred to as the hybridization complex, is recovered from the sample mixture. This recovery is carried out by adding to the mixture containing hybridization complexes a solid substrate which is coated with a polynucleotide complementary to the tail of the capture probe. The tail of the capture probe present in the hybridization complex hybridizes with the complementary substrate, making it possible to separate the entire hybridization complex from the sample. In the case of pre-hybridized capture probes, the substrate containing the attached probe is removed from the sample mixture. Intact hybridization complexes may be released from the solid substrate by treatments which reversibly disrupt base pairings (the capture probe forms fewer base pairs with the solid substrate than do the probes with the target transcript) and complexes may be recaptured on to other solid substrates; the result of this cycling of hybridization complexes is reduction of noise which usually binds non-specifically to the solid substrate.

The quantity of detector probes and, thus, of the specific HPV transcript, present on the separated substrate can then be determined using known techniques, such as scintillation counting, densitometric scans of autoradiographs, fluorescence spectroscopy, and beta emission counters (e.g., Betagen). The method used will depend upon the detector probe label. The amount of signal is related to the amount of target nucleic acids captured, which in turn is proportional to the amount of transcript in the sample. The amount of transcript is related to the level of transcriptional activity of the selected gene (e.g., E6/E7 genes), which activity is indicative of the neoplastic risk. Thus, the method provides a sensitive assay for determining the risk of progression of HPV infection to serious CIN or CIS.

In the embodiment of the present invention in which the occurrence (presence or absence) of selected HPV types is determined or quantitated in order to assess risk of progression to serious cervical dysplasia or cancer in situ, the procedure is as follows: as described above, the presence or absence and/or quantity of one or more selected HPV types is determined. These types can be high-oncogenic HPV types, low-oncogenic types or both. The results of this assessment are compared with a previously-established relationship between the HPV types detected or quantitated and risk of progression to serious dysplasia of the cervix or to cervical carcinoma. Such a relationship can be determined by using the previously-described method of detecting and/or quantitating selected HPV types in women whose clinical characteristics (e.g., extent of progression of the condition) is also assessed and related to patterns of HPV DNA present and/or patterns of transcription.

HPV-Specific Nucleic Acid Probes

Nucleic acid probes and probe sets which are specific for HPV genes associated with cervical cytologic abnormalities which often progress to more serious CIN or CIS, are used in the present method. Probes which are particularly useful in the present method are oligonucleotide probes having a nucleotide sequence which is complementary to at least a portion of the E6 and/or E7 ORF, or spliced portions thereof. A nucleotide sequence is complementary to a second or target nucleotide sequence (e.g., the E6 or E7 gene of HPV) if it hybridizes and remains hybridized to the second or target nucleotide sequence under the conditions used in the method.

Figure 2:
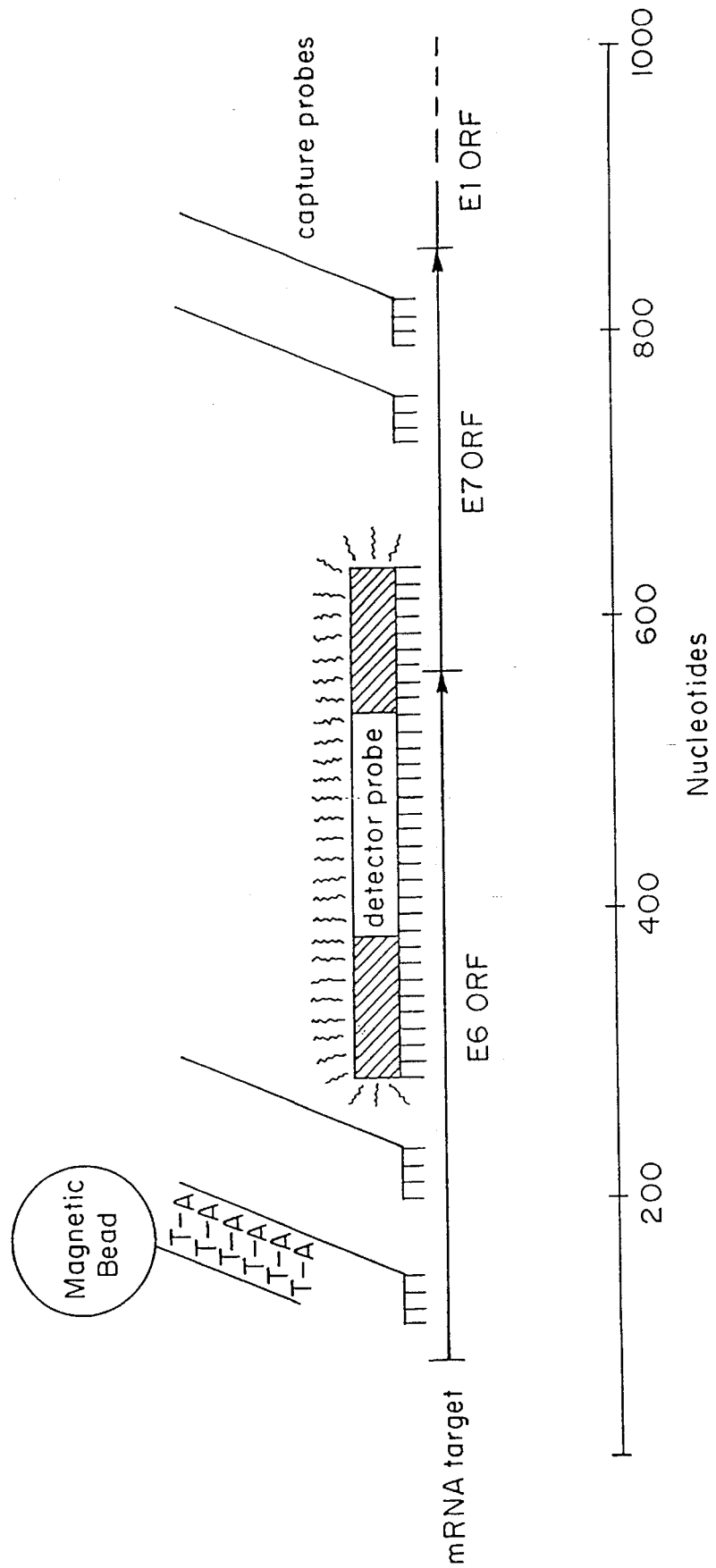
FIG. 2 is a schematic illustration of the hybridization complex of mRNA targets, d(A)-tailed oligonucleotide capture probes, and radiolabeled detector probes for detection of E6/E7-containing transcripts of HPV.

Two types of probes are used: tailed oligonucleotide "capture probes" and labelled "detector probes" (also referred to as labelled riboprobes). Tailed capture probes serve two purposes: they are complementary to/hybridize to at least a portion of the ORF sequence of a gene of a selected HPV type or of the encoded transcript (mRNA) and they link the hybridization complex (capture probe/target nucleotide sequence/detector probe) to a solid support, thus making it possible to separate the hybridization complex from the remainder of the sample. A schematic representation of the complex of detector probe, target transcript, capture probes and solid support is shown in FIG. 2. Labelled detector probes are generally single-stranded RNA or DNA probes which hybridize to portions of the bi- or polycistronic transcripts of genes of selected selected HPV types; specifically, they hybridize to portions of these genes which can be, but preferably are not also recognized by the capture probes. The selected HPV types are either high-oncogenic or low-oncogenic.

The capture probes are characterized by a polynucleotide tail which is generally formed from a nucleotide homopolymer, such as polydeoxyriboadenylate (poly(dA)), polydeoxyribocytidylate (poly(dC)), polydeoxyriboguanylate (poly(dG)), and polydeoxyribothymidylate (poly(dT)). The probe tail is complementary to a polynucleotide sequence which is affixed to a solid support, such as magnetic beads, polystyrene beads and polystyrene dipsticks, allowing the probe to be captured and separated from the test sample.

Probes particularly useful in the present invention as capture probes have the following characteristics:

1. They are synthesized easily by in vitro transcription (for detector probe) or by chemical means (for oligonucleotide capture probes). Detector probes should be easily labeled, and to high specific activities, during in vitro transcription or chemical synthesis or by post-synthetic modification with either isotopic or non-isotopic markers which can be easily quantitated.

2. They are HPV type-specific. Although HPV 6 sometimes has been associated with carcinomas, it and HPV 11 most often are associated with low risk for progression to high grade dysplasia. Because E6 and E7 genes of HPV 6 and HPV 11 show high sequence conservation, probes to these regions may cross-hybridize; this result would not detract from the efficacy of the assay. Probes which are particularly useful in the present assays are those specific for HPV 16, 18, 31, 33 and 35.

3. They are of sufficient length and nucleotide sequence that they do not dissociate from specific target sequences on viral transcripts in the assay format, and hybridize specifically and quantitatively to transcripts of HPV.

4. They hybridize to selected HPV DNA sequences or transcripts of selected types of HPV. Target transcripts contain at least a portion of the ORF to allow for stable hybridization of the detector probes and at least one capture probe. Probes are designed in such a manner that efficiency of hybridization of probes to target transcripts is not diminished by excision of introns from transcripts (e.g., formation of E6*I and E6*II).

5. The integrity of probes used is maintained in the conditions of the assay.

Oligonucleotide probes which are particularly useful as capture probes in the present invention are poly-(dA)-tailed oligonucleotide probes, such as those prepared according to the method described by M. L. Collins in European Patent Application 0265244, filed Oct. 21, 1987, the teachings of which are incorporated herein by reference. Capture probes which are prehybridized to a solid substrate also can be used. Prehybridized probes are described in detail by M. L. Collins et al. in co-pending U.S. patent application Ser. No. 07/902,517 filed Mar. 10, 1989, the teachings of which are incorporated herein by reference.

The second type of probe used in the present method is a riboprobe or detector probe whose sequence is specific for an HPV transcript or selected HPV DNA, and which generally have a detectable label, such as a radionuclide, or fluorescent indicator. Detector probes are used to quantitate the DNA or mRNA. Detector probes can be prepared by art recognized techniques. Detector probes are generally single stranded RNA probes which hybridize to bi- or polycistronic transcripts of a selected HPV gene, such as the E6 or E7 gene. The detector probes are preferably labeled with a radionuclide, such as $^{32}P$ or $^{125}I$, but can be labeled by any means which does not interfere with the ability of the detector probes to hybridize to complementary sequences and which can be detected using available techniques.

The present assay system and method of using it can be incorporated into a kit for clinical use. Such a kit includes a sample processing solution containing a chelating agent, such as EDTA, and an agent for disrupting molecular structures (e.g., membranes) of cells (e.g., a chaotropic agent); the tailed capture probes and labelled detector probes; at least one buffer; an agent for inhibiting RNAase enzymes (to prevent degradation of the target transcripts); a solid support (e.g., magnetic beads or polystyrene substrate) coated with a polynucleotide which is complementary to the capture probe tail; reference or standard nucleic acids to be run simultaneously with the sample as a control; and a wash buffer containing a detergent and an agent (e.g., a chaotropic agent) for disrupting molecular structures of cells. The kit can optionally contain additional wash buffers, a means for detecting the labelled detector probe, one or more elution buffers, amplification or cloning reagents and/or additional positive control samples or negative control sample. Amplification of the target sequences, if desired, can be accomplished, for example, by the technique described by Mullis in U.S. Pat. No. 4,683,202. Amplification of the detector probe, after it has been cycled with the hybridization complexes, and/or cloning of the target sequences, can be accomplished, for example, by the method described by Maniatis et al. in *Molecular Cloning: A Laboratory Manual*, Cold Spring Harbor Laboratory, Cold Spring Harbor, N.Y. (1982).

The invention will now be further illustrated by the following Exemplification.

EXEMPLIFICATION

Design, Preparation, and Physical Description of Probes

HPV type-specific oligonucleotide capture probes, about 40 nucleotides long are shown in FIG. 3. The Wordsearch/ Segments Programs of the University of Wisconsin Suite was used to identify regions of HPV genomic, sense strands (i.e., RNA sense) which might hybridize to these 33 oligonucleotide probes, and results of these analyses are shown in the Table.

TABLE

Predicted Number of Base Pairs Between Oligonucleotide Probes and Discreet Regions of HPV Genomes

| HPV Type | Probe No. | Probe Length | ORF | Nts Recognized By Probe | 6 | 11 | 16 | 18 | 31 | 33 | 35 |
|---|---|---|---|---|---|---|---|---|---|---|---|
| 6 | 6-1 | 40 | E6 | 111–150 | 40 | 34 | <20 | NF | 24/4 | <20 | NF |
|   | 6-2 | 39 | E6 | 167–205 | 39 | 30 | 23/8 | NF | 25/1 | 22/6 | NF |
|   | 6-3 | 32 | E7 | 644–675 | 32 | 25 | 23/6 | <20 | <20 | NF | NF |
|   | 6-4 | 36 | E7 | 715–750 | 36 | 30 | 21/4 | 22/1 | <20 | NF | NF |
|   | 6-5 | 36 | E7 | 761–796 | 36 | 21/10 | NF | NF | 22 | NF | NF |
| 11 | 11-1 | 40 | E6 | 112–151 | 34 | 40 | <20 | <20 | <20 | NF | NF |
|   | 11-2 | 40 | E6 | 152–191 | 33 | 40 | NF | NF | 22/1 | 22/8 | NF |
|   | 11-3 | 40 | E7 | 561–600 | 36 | 40 | <20 | <20 | 24/2 | 20/3 | NF |
|   | 11-4 | 40 | E7 | 669–708 | 37 | 40 | NF | 23/4 | <20 | <20 | NF |
|   | 11-5 | 36 | E7 | 715–750 | 30 | 36 | <20 | 23/8 | <20 | NF | NF |
|   | 11-6 | 40 | E7 | 755–794 | 31 | 40 | 20 | 25/2 | <20 | NF | NF |
| 16 | 16-1 | 38 | E6 | 96–133 | <20 | 23 | 38 | NF | <20 | NF | 22 |
|   | 16-2 | 40 | E6 | 150–189 | <20 | NF | 40 | <20 | 22/3 | 20/1 | NF |
|   | 16-3 | 40 | E7 | 701–740 | <20 | <20 | 40 | 21/4 | 32 | 29 | 30 |
|   | 16-4 | 40 | E7 | 747–786 | <20 | 40 | 21/4 | <20 | <20 | NF |
|   | 16-5 | 40 | E7 | 787–826 | 26/1 | 20 | 40 | <20 | 32 | 22/2 | NF |
| 18 | 18-1 | 38 | E6 | 103–140 | NF | NF | <20 | 38 | <20 | NF | NF |
|   | 18-2 | 40 | E6 | 157–196 | 21/3 | <20 | NF | 40 | 23/3 | <20 | NF |
|   | 18-3 | 41 | E7 | 627–667 | NF | NF | <20 | 41 | 23/2 | 20/4 | NF |
|   | 18-4 | 38 | E7 | 752–789 | <20 | <20 | <20 | 38 | <20 | <20 | NF |
|   | 18-5 | 40 | E7 | 796–835 | 25 | <20 | 27/3 | 40 | <20 | NF | NF |
|   | 18-6 | 40 | E7 | 836–875 | <20 | <20 | NF | 40 | 20 | NF | NF |
| 31 | 31-1 | 40 | E6 | 103–142 | 23 | 24/4 | NF | 21/3 | 40 | NF | NF |
|   | 31-2 | 40 | E6 | 145–183 | <20 | <20 | <20 | <20 | 40 | <20 | NF |
|   | 31-3 | 37 | E7 | 721–757 | NF | <20 | 21/2 | NF | 37 | <20 | NF |
|   | 31-4 | 40 | E7 | 763–802 | <20 | NF | <20 | NF | 40 | NF | 31 |

TABLE-continued

| | | | | Predicted Number of Base Pairs Between Oligonucleotide Probes and Discreet Regions of HPV Genomes | | | | | | |
|---|---|---|---|---|---|---|---|---|---|---|
| HPV Type | Probe No. | Probe Length | ORF | Nts Recognized By Probe | 6 | 11 | 16 | 18 | 31 | 33 | 35 |
| | 31–5 | 39 | E7 | 815–853 | NF | NF | 28 | <20 | 39 | 20 | 28 |
| 33 | 33–1 | 40 | E6 | 124–163 | NF | <20 | 22 | 21/1 | 26 | 40 | 24 |
| | 33–2 | 41 | E6 | 164–204 | NF | 20/2 | <20 | 20/2 | <20 | 41 | 22/2 |
| | 33–3 | 40 | E7 | 602–641 | <20 | 30/3 | 30 | <20 | 31 | 40 | 33 |
| | 33–4 | 40 | E7 | 713–752 | <20 | 24/8 | NF | NF | 26/3 | 40 | NF |
| | 33–5 | 37 | E7 | 756–792 | 20/4 | <20 | <20 | NF | 23/3 | 37 | NF |
| | 33–6 | 40 | E7 | 798–837 | 27/6 | 24/2 | 22/6 | <20 | 21/2 | 40 | 25/2 |
| 35 | 35–1 | 39 | E6 | 111–149 | NF | NF | 22 | NF | NF | 20 | 39 |
| | 35–2 | 41 | E6 | 153–193 | NF | NF | NF | NF | NF | 26 | 41 |
| | 35–3 | 39 | E7 | 740–778 | NF | NF | NF | NF | NF | NF | 39 |
| | 35–4 | 39 | E7 | 780–818 | NF | NF | 32 | NF | 30 | NF | 39 |
| | 35–5 | 39 | E7 | 829–867 | NF | NF | 31 | NF | 30 | NF | 39 |

Numbers in the Table refer to the base pairs in a discreet region of the viral genome which are predicted, from computer analyses (algorithm of Wilbur and Lipman; P.N.A.S. 80:726–739, 1983)), to pair with portions of the oligonucleotides. Numbers after slash marks (/) indicate the gaps that would be needed in the oligonucleotide or target sequence to allow for the number of base pairs. For each HPV type, the nucleotide sequences (GenBank designations) that are covered by each type-specific oligonucleotide are shown. In some cases, the computer program did not find any likely regions of significant base pairing between the oligonucleotide sequences and genomic sequences; these cases are noted "not found" (NF). The oligonucleotides in Table 1 are unlikely to form stable hybrids with other types of HPV, therefore, they are considered to be type-specific.

Design of Exon-Specific Capture Probes for HPV 16, HPV 18, HPV 31, HPV 33 and HPV 35

Figure 4:
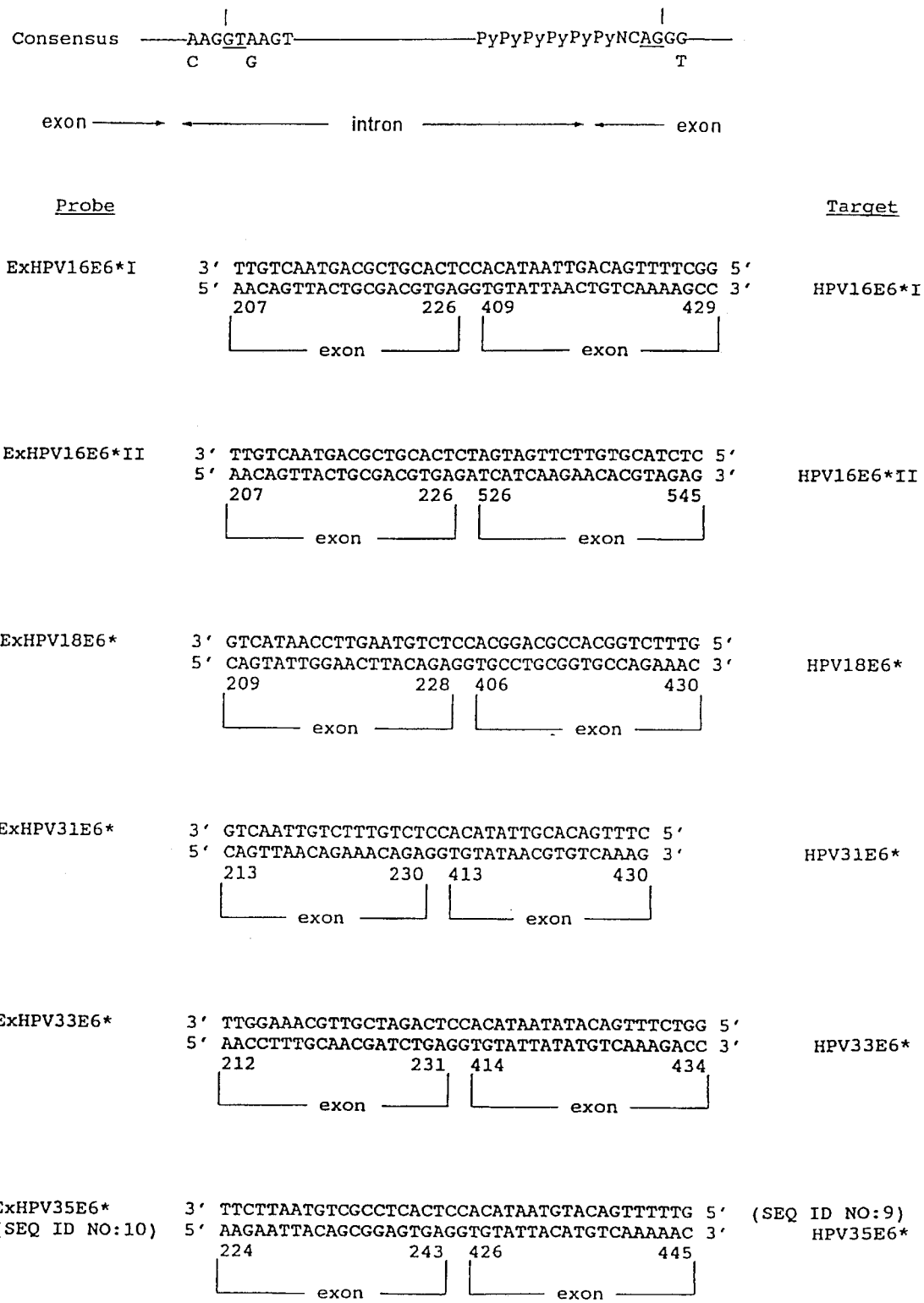
FIG. 4 shows nucleotide sequences and target sites of probes for type-specific detection of spliced E6 transcripts (E6*) of HPV 16, HPV 18, HPV 31, HPV 33 and HPV 35. Predicted base pairs between spliced E6* transcripts and specific oligonucleotide probes which span the upstream and downstream exons are shown.

Splice junction sequences in the E6 ORF have been identified in several oncogenic types of HPV, including HPV 16, HPV 18, HPV 31, HPV 33, and HPV 35 but they are not present in the E6 ORF's of HPV 6 and HPV 11. These splice donor and acceptor sites are utilized in HPV 16 and HPV 18, as is demonstrated by the presence of spliced mRNA's (determined by sequencing cDNA's) in carcinoma cell lines. The presence of spliced transcripts can be used as predictors of progression to more serious disease. Thus, splice-junction capture probes which are predicted to form stable hybrids only with spliced transcripts were designed. Approximately 20 nucleotides of each capture probe hybridize to the 3' end of the upstream exon and the remaining 20 nucleotides hybridize to the 5' end of the downstream exon. Sequences of these probes and their target sites on transcripts are shown in FIG. 4. Analyses of the alignment (algorithm of Wilbur and Lipman) of splice-junction probes and the genomes of HPV 6, HPV 11, HPV 16, HPV 18, HPV 31, and HPV 33 revealed that each probe is predicted to hybridize only to the transcripts of the HPV type for which the probe was designed. Different probes were designed for detection of each of the two E6 spliced mRNA's (E6*I and E6*II) of HPV 16.

Figure 5:
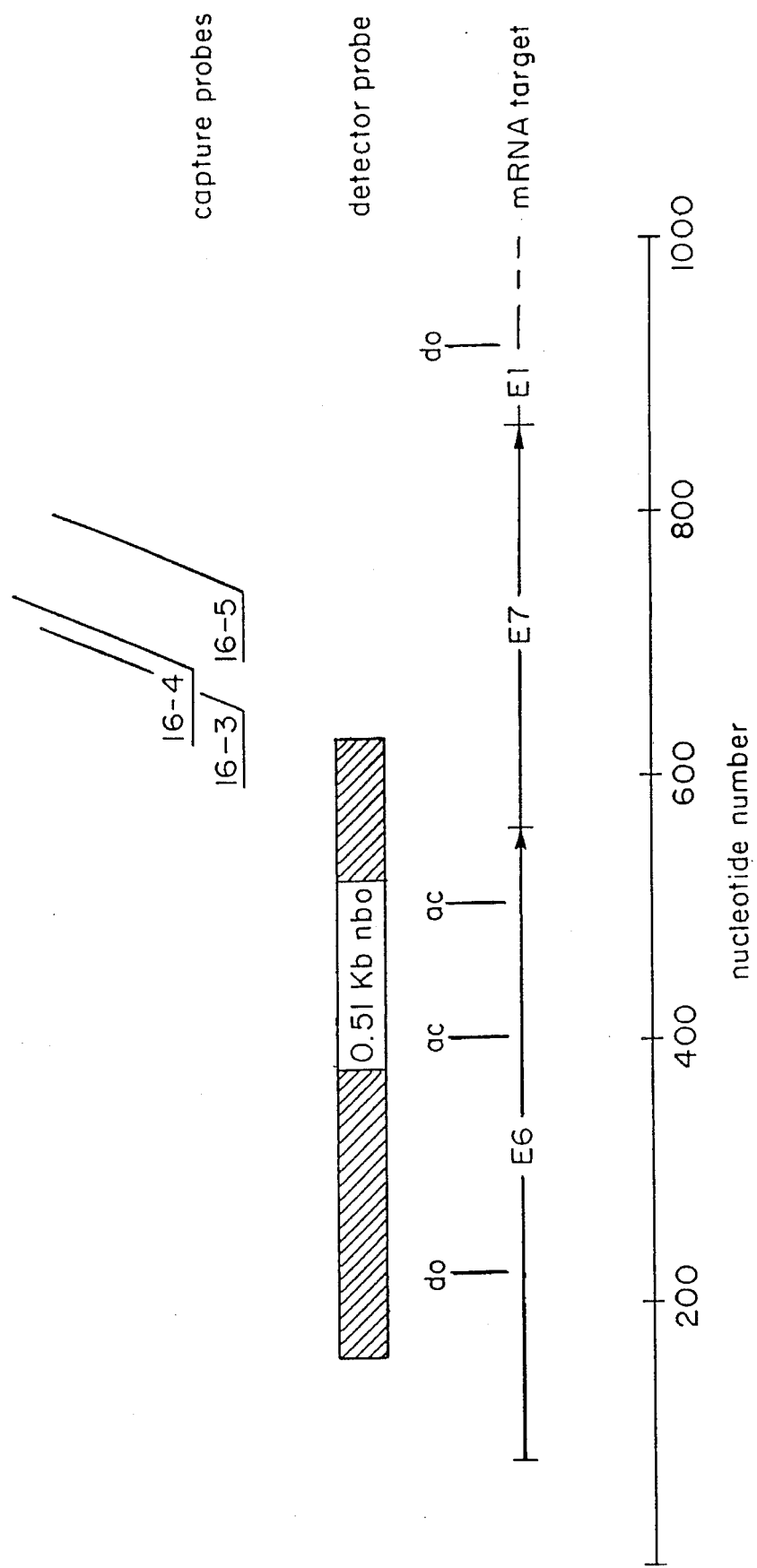
FIG. 5 is a schematic illustration of capture and detector probes on E6/E7 transcripts of HPV 16, showing the specific arrangement of probes on mRNAs of HPV 16. Splice donor (do) and acceptor (ac) sites in the E6 ORF are indicated.

Design of HPV 16-Specific Capture Probes and Arrangement of Probes in the HPV 16 Assay Ten HPV 16-specific oligonucleotide probes (about 40 nucleotides long) were designed and tested in the assay, described below. Three of these probes, designated 16-3, 16-4, and 16-5, were adapted for use in the assay because they afforded high sensitivity and specificity. The placement of these three probes with respect to the RNA target and the detector probes is shown in FIG. 5. Capture probe 16-3, the probe closest to the detector probe, hybridizes to target sequences 46 nucleotides beyond the 3' end of the hybridization site covered by the detector riboprobe. Therefore, after hybridization of the detector probe to mRNA, only a short portion remains single stranded (i.e., not covered by capture or detector probes), thus minimizing the chances for degradation by RNases.

The alignment of these capture probes with sequences in HPV 6, HPV 11, HPV 16, HPV 18, HPV 31, HPV 33 and HPV 35 is shown in FIG. 6. Inspection of potential base pairs between these probes and the other genital HPV types, an alignment that was made by visual and computer analyses, reveals that base mismatches (not underlined) are numerous and approximately evenly distributed along the capture probes. As a result, these hybrids would be very unstable.

The 3' ends of capture probes are extended by sequential addition of d(A) residues with terminal transferase such that the final poly-d(A) "tail" is 150–200 nucleotide long, the minimum length that will allow unencumbered capture of the hybridization complex to d(T)-modified magnetic beads.

Design and Preparation of HPV 16-Specific Detector Riboprobe and Target RNA

Figure 7:
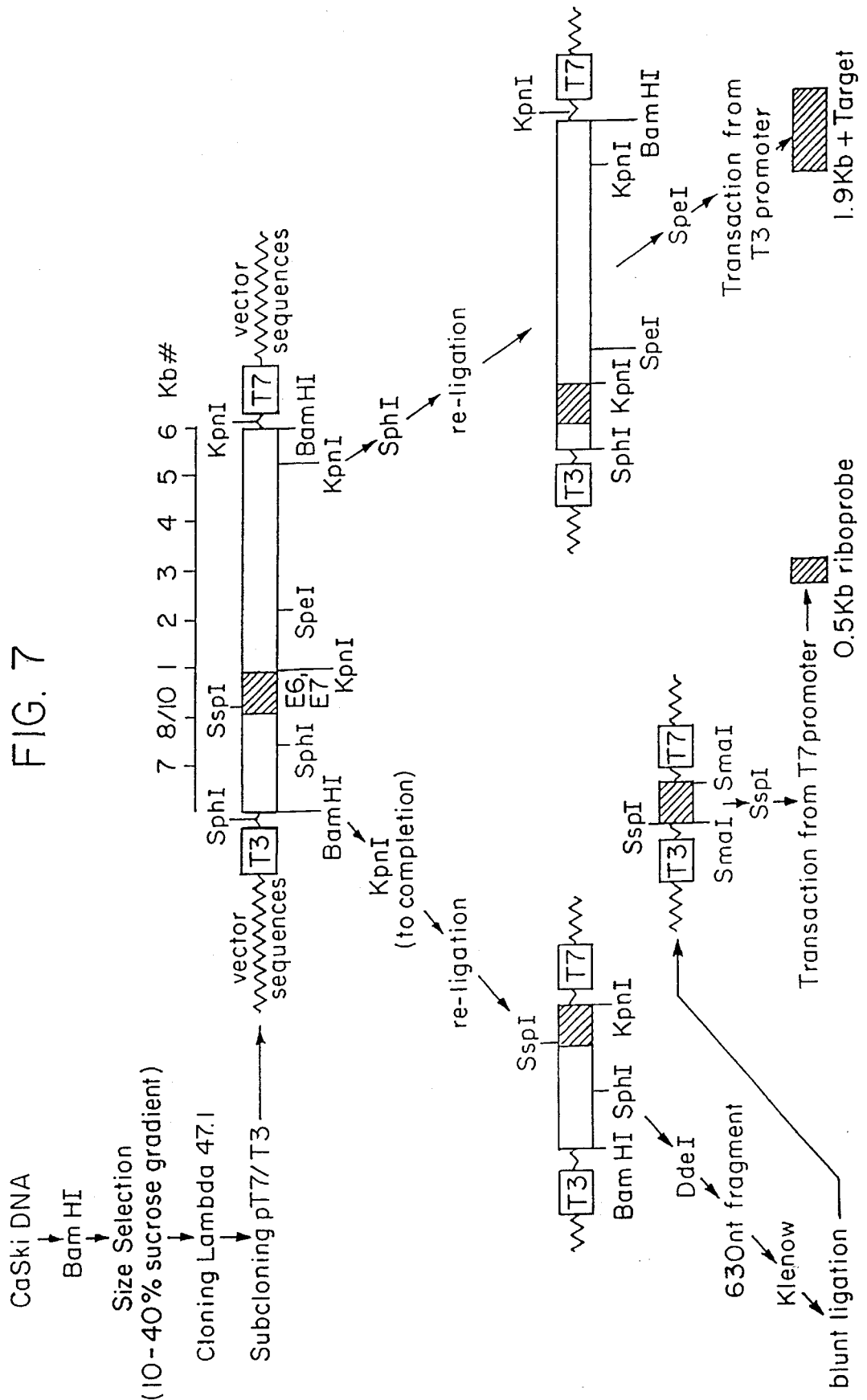
FIG. 7 is a schematic illustration of the steps for cloning HPV 16 DNA into lambda 47.1 and construction of recombinant molecules for synthesis of detector probes and positive target transcripts. The strategy for engineering a construct for production of the HPV 16 riboprobe is shown on the left side of the figure and the construction of a recombinant molecule for synthesis in vitro of mRNA molecules which contain the E6 and E7 ORF's (i.e., positive target transcripts) is shown on the right side of the figure.

HPV 16 DNA was cloned from CaSki cells, known to contain HPV 16 genomes (Baker et al., J. Virol., 16(4): 962–971, 1987), into lambda 47.1 from which it was subcloned into the pT7/T3α-18 plasmid (Bethesda Research Laboratory). A summary of the cloning/subcloning scheme is shown in FIG. 7. A 630 nucleotide Dde I fragment (nucleotides 25–655; Seedorf et al., Virol., 145:181–185, 1985) was excised, end-filled, and subcloned into Sma I-restricted pT7/T3α-18 plasmid. Sequence analysis, obtained by double or triple reads in most cases, revealed that the insert contained only nts 25–655 of the HPV 16 genome. In vitro transcription with T7 polymerase on this construct, linearized with Ssp I restriction endonuclease, results in a single product with a homogeneous electrophoretic mobility and an apparent size of 0.5 Kb, that should hybridize to the 3' three-fourths of the E6 ORF and the 5' third of the E7 ORF. The detector probe contains, in addition to 471 nucleotides of the HPV 16 sequence, 22 additional nucleotides of the plasmid sequence on its 5' end, a result of transcription initiation on the T7 promoter and procession through a portion of the multiple cloning site in the vector. These additional 5' nucleotides will not interfere with hybridization of the capture probes, the most proximal being 46 nucleotides away. The detector probe, after hybridization to target mRNA, should extend about 40 nucleotides 5' to the splice donor site at nucleotides 224–232 (FIG. 5); this hybrid is predicted to be very stable. Excision of either of the E6 introns would result in mRNA molecules that base pair with either 162 or 288 nucleotides of the detector probes. These hybrids should be stable in the assay. Following the manufacturers' instructions for synthesis of transcripts with T7 polymerase, $^{32}$P-labeled riboprobes with specific activities of $5\times10^8$ cpm/µg are produced. Placement of the detector probe on E6/E7 transcripts was designed such that E6/E7 target sequences flanking the hybridization site of the detector riboprobe would be available for hybridization to capture probes.

The sensitivity of the HPV 16 assay was also determined. For this purpose it was important to produce, by in vitro transcription, well characterized positive targets (i.e., mRNA-like molecules which contain the ORF's of the E6 and E7 genes). Transcription from the T3 promoter in the construct which contained full length genomic HPV 16, revealed a putative transcription terminator just upstream from the E6 and E7 genes (nucleotides 7400–7600 in the non-coding region). Visual inspection of the sequences in this region, which lies just downstream from a polyadenylation signal, suggests that transcription of plus-sense RNA from this portion of the genome would produce RNA's which have numerous stretches of U residues, characteristics of transcription terminator; therefore, a 1.3 Kb Sph I fragment which includes about half of the region rich in termination sequences and a few sequences in the vector was deleted. Transcription from the resulting construct (linearized with Spe I) with T3 polymerase yields one expected major transcript of 1.9 Kb as well as a shorter minor RNA species (about 600 nucleotides shorter than the major one). The 1.9 Kb transcript was used as a positive target in the assay.

Design and Performance of the HPV 16 Assay

Preparation of samples and procedures for performance of the assay are the same as those described by M. Collins in European Patent Application, Number 0265244, the teachings of which are incorporated herein by reference. In brief, cells from cervical specimens (e.g., cervical lavage, scrapes, biopsies, and tumors) are mixed with sample processing buffer (SPB), containing 5M guanidinium isothiocynate (GuSCN) and 0.1M ethylenediaminetetraacetic acid (EDTA) in order to solubilize the cells and sample matrix and to inhibit RNAses. Samples are diluted such that the final concentration of GuSCN is 2.5M and incubated with 67 ng/ml of each capture probe and $1.4\times10^7$ cpm/ml of detector probe at 37° for 2–18 hours. Then, d(T)-coated magnetic beads are added (final concentration of 0.125% solids) and the resulting mixture is incubated at 37° for 15 minutes; d(A)-tailed capture probes hybridize to the d(T)-coated magnetic beads during this period. Wash buffer (0.5M GuSCN, 40 mMTris-HCl, pH 7.8, 10 m MEDTA, 0.5% sarkosyl, 0.2% bovine serum albumin, and 0.1% antifoam) is added to the mixture and the magnetic beads then are concentrated on the walls of the tubes by a magnetic field. The supernatant fluid is aspirated. Beads are washed two additional times with wash buffer, following the procedure just described, and then re-suspended in a buffer containing 3.25M GuSCN, 100 mM Tris-HCl, pH 7.8, 65 mM EDTA, 0.5% BSA, and 0.5% sarkosyl. Following incubation of the suspension at 37° for 10 minutes, nucleic acid complexes should be released from the beads due to disruption of the A-T bonds between the poly-d(A) tails of the capture probes and the oligo-d(T) chains of the magnetic beads. After concentration of the magnetic beads on the tube walls by a magnetic field, the release buffer and nucleic acid complexes are transferred to another tube and hybridization complexes are captured on a second set of magnetic beads, following the procedure just described. This capture, release, and re-capture of the nucleic acid complexes on magnetic beads is called reversible target capture.

A second round of reversible target capture is performed and nucleic acid complexes in the release buffer are captured on a third set of beads. After the beads are washed once, they are resuspended in wash buffer and an aliquot of the suspension is applied to a nitrocellulose membrane. Radioactivity can be detected by exposure of the membrane to film or by quantitation of counts on a beta emission blot analyzer (e.g., Betagen). Exposure of the film may be quantitated on a densitometer. Alternatively, fluorescein-labeled detector oligonucleotides or riboprobes may be used in the assay.

Figure 8B:
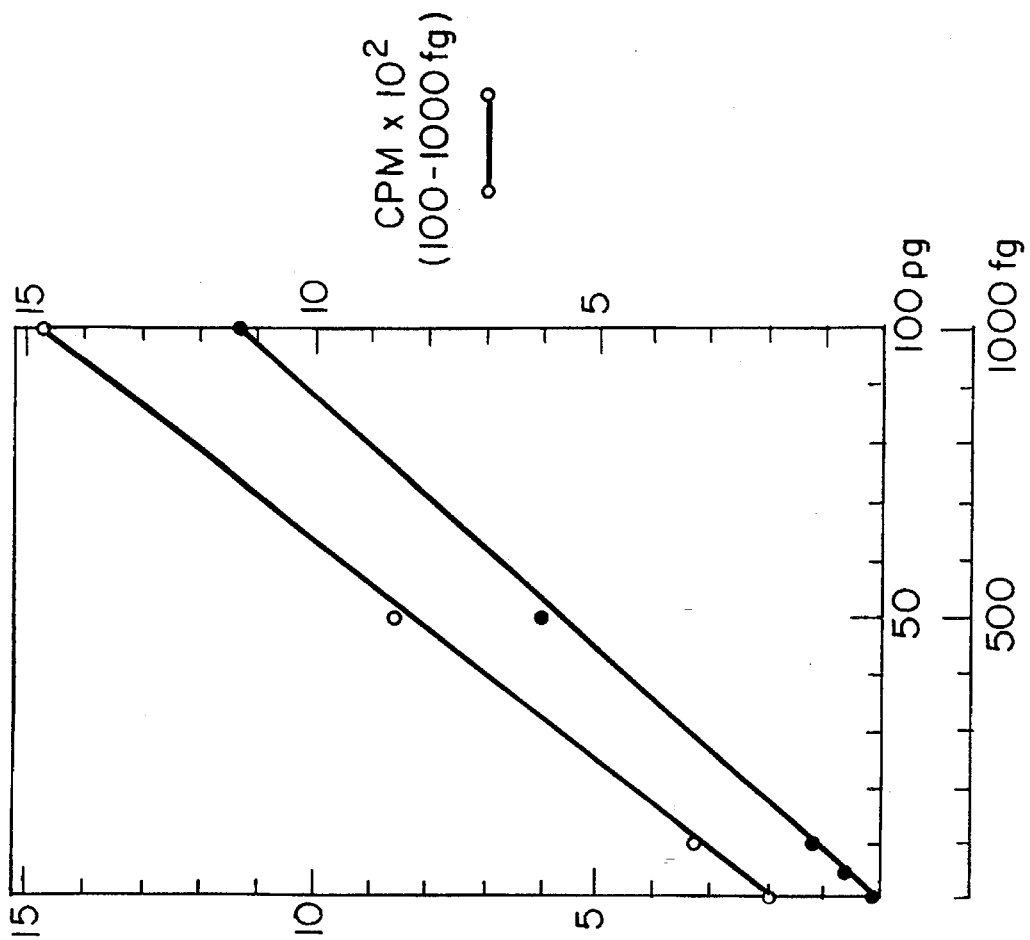
FIG. 8A and 8B show the relationship between the concentration of positive target and signal in an HPV 16 assay.
Figure 8A:
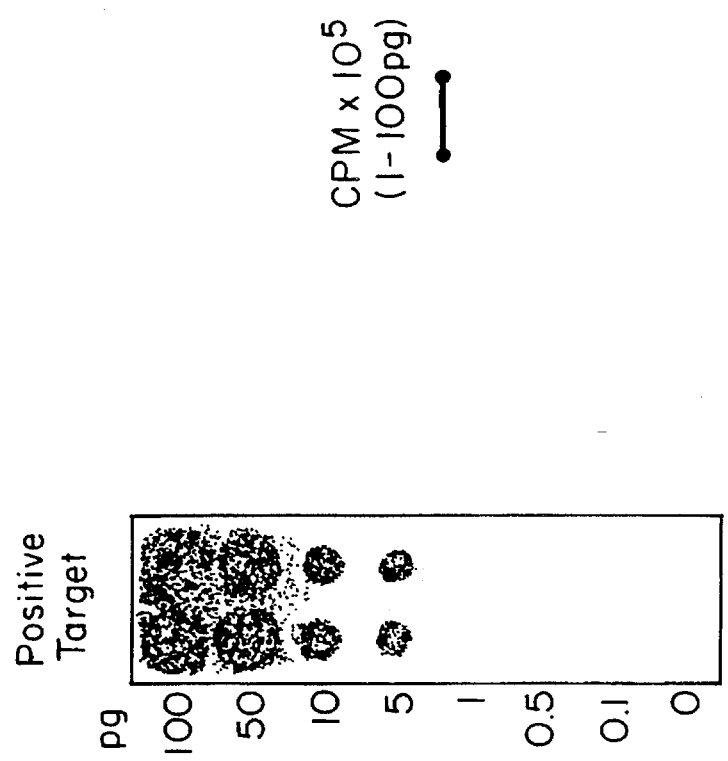

Efforts were made to quantitate the sensitivity of the HPV 16 assay using in vitro-generated positive target transcripts. Examination of the X-ray film revealed (FIG. 8A) that 500 fg of target (500,000 molecules) could be visualized and that a signal was not detected if target RNA was omitted; no signal was detected if lysates from 200,000 HeLa cells (which contain HPV 18 sequences) are used in the assay. A standard curve, produced by plotting radioactivity on beads vs. amount of positive target RNA, is a straight line for RNA target values of 100 fg to 100 pg (FIG. 8B).

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A nucleic acid probe selected from the group consisting of probes 6-2, and 6-4 as shown in FIG. 3, said probe hybridizes specifically to nucleic acid from HPV type 6 in cervical specimens.

2. A nucleic acid probe selected from the group consisting of probes 11-3, 11-4 and 11-5 as shown in FIG. 3, wherein said probe hybridizes specifically to nucleic acid from HPV type 11 in cervical specimens.

3. A nucleic acid probe selected from the group consisting of probes 16-1, 16-2 and 16-5 as shown in FIG. 3, said probe hybridizes specifically to nucleic acid from HPV type 16 in cervical specimens.

4. A nucleic acid probe selected from the group consisting of probes 18-1 and 18-2 as shown in FIG. 3, said probe hybridizes specifically to nucleic acid from HPV type 18 in cervical specimens.

5. A nucleic acid probe selected from the group consisting of probes 31-1, 31-2, 31-3, 31-4 and 31-5 as shown in FIG.

3, said probe hybridizes specifically to nucleic acid from HPV type 31 in cervical specimens.

6. A nucleic acid probe selected from the group consisting of probes 33-1, 33-2, 33-3 and 33-4 as shown in FIG. 3, said probe hybridizes specifically to nucleic acid from HPV type 33 in cervical specimens.

7. A nucleic acid probe selected from the group consisting of probes 35-1, 35-2, 35-3, 35-4 and 35-5 as shown in FIG. 3, said probe hybridizes specifically to nucleic acid from HPV type 35 in cervical specimens.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:

(A) LENGTH: 39 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:1:

TAAGGTCGTT CAGCTGGGTC CTGAAACATA CCGCACCTT 39

(2) INFORMATION FOR SEQ ID NO:2:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:2:

CATGGATGCT TTCTTCTACC TCGTTGCACA AATCATGCAG T 41

(2) INFORMATION FOR SEQ ID NO:3:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

CACAGACGTA GTGTCGCCTC ACATTTACAA CAGGACGTT 39

(2) INFORMATION FOR SEQ ID NO:4:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

ATCTTCCAAT TTACGTATGT CAATGTGTGT GCTCTGTACT 40

(2) INFORMATION FOR SEQ ID NO:5:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

CTCTCTGTGA ACAGCCGGGG CACACTATTC CAAATGTGCT 40

(2) INFORMATION FOR SEQ ID NO:6:

(i) SEQUENCE CHARACTERISTICS:
(A) LENGTH: 40 base pairs
(B) TYPE: nucleic acid
(C) STRANDEDNESS: single
(D) TOPOLOGY: linear -continued ( i i ) MOLECULE TYPE: DNA (genomic)

( x i ) SEQUENCE DESCRIPTION: SEQ ID NO:6:

CAGACACCTC CAATTATAAT ATTGTAACGT CCTGTTGTAA 40

( 2 ) INFORMATION FOR SEQ ID NO:7:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GGCGACACTA CGTCTGTGTG TACAGAGCAC ACACATTGAC 40

( 2 ) INFORMATION FOR SEQ ID NO:8:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

ATACGTAAAT TGGAAGATTT ATTAATGGGC ACATTTGGAA 40

( 2 ) INFORMATION FOR SEQ ID NO:9:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GTTTTTGACA TGTAATACAC CTCACTCCGC TGTAATTCTT 40

( 2 ) INFORMATION FOR SEQ ID NO:10:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

AAGAATTACA GCGGAGTGAG GTGTATTACA TGTCAAAAAC 40